United States Patent [19]
Armstead

[11] Patent Number: 6,028,241
[45] Date of Patent: *Feb. 22, 2000

[54] PATIENT UNDERPAD

[76] Inventor: Kenneth W. Armstead, 634 Powell Grove Rd., Lebanon, Tenn. 37090

[*] Notice: This patent is subject to a terminal disclaimer.

[21] Appl. No.: 09/104,131

[22] Filed: Jun. 24, 1998

[51] Int. Cl.⁷ ...................................................... A61F 13/15
[52] U.S. Cl. ........................ 604/367; 604/358; 604/378; 604/384
[58] Field of Search .................................. 66/196; 2/170, 2/195.2, 16; 428/138, 198, 284; 604/367, 358, 378, 384

[56] References Cited

U.S. PATENT DOCUMENTS 4,772,281  9/1988  Armstead .
4,943,286  7/1990  Armstead .

*Primary Examiner*—John G. Weiss
*Assistant Examiner*—Miley C. Peppers, III
*Attorney, Agent, or Firm*—Waddey & Patterson; Mark J. Patterson

[57] ABSTRACT

A washable and re-usable patient underpad has top section of a porous terry or circular knit fabric with a polyester stabilizing yarn. The top section is serged, stitched, or bonded to a bottom section that includes a PVC vinyl water barrier bonded to a polyester knit cloth. The loops of the terry or circular knit fabric layer are preferably oriented toward the bottom section to enhance air circulation through the pad.

15 Claims, 1 Drawing Sheet

PATIENT UNDERPAD

BACKGROUND OF THE INVENTION

The present invention relates generally pads used by hospitals and nursing homes to protect bedding and bedridden patients who may be incontinent.

More particularly, this invention pertains to a washable and reusable patient underpad constructed from multiple fabric layers to provide a more comfortable patient contact surface and improved cleaning and durability characteristics.

Reusable patient underpads were relatively unknown until a few years ago. They have gained popularity due to the rising costs associated with incontinence products and the effort to decrease the use of disposable items which must accumulate in landfills or be incinerated. The effectiveness of patient underpads is judged by a number of criteria, including resistance to leakage, staying in place, dry comfort, wet comfort, wrinkling and rucking, product size, aesthetics, odor, effects on skin, effectiveness as a lifting and turning aid and overall acceptability. Norris, et al. (1993), "Underpad Overview," *Nursing Times* 89(21): 68–74.

In a British study, 72 subjects tested found wet comfort and leakage resistance to be the most important characteristics of a patient underpad. Id. In a 1996 study of urinary incontinence in residential and nursing homes for the elderly, 39 percent of the residents had severe symptoms of urinary incontinence resulting in bed-wetting of clothing. In these institutions, the lack of absorbency of presently used patient underpads contributes to increased costs due to the spread of body fluids from the surface of the patient underpad to the surrounding bedding and bed linens. Peet, et al. (1996), "The Management of Urinary Incontinence in Residential and Nursing Homes for Older People," *Age and Ageing* 25(2): 139–143.

Patient underpads are often used for individuals who experience long periods of confinement to bed. In these circumstances, surface wetting, combined with the warmth of the human body, contribute to the growth of microorganisms which may pose a health hazard to the patient.

Underpads are made of woven and non-woven materials which provide little, if any, cushioning for the bedridden patient who may develop decubitus ulcers at sites where pressure on the skin and underlying tissue is greatest. Tissues weakened by the effects of extended periods of bed rest may be easily damaged, and may be easily abraded by fabrics which, particularly when wet, have a higher coefficient of friction.

Of the underpad constructions currently available commercially, one of the most successful has been a needle-bond non-woven fabric layer combined with a woven or brush trico quilted top.

U.S. Pat. No. 4,772,281 issued to K. Armstead on Sept. 20, 1988, discloses an improved patient underpad that does not breakdown after repeated washings. The pad disclosed by that invention successfully stood up to 300 washings or more. However, after use and experimentation with this pad, it was found that the pad could become rougher over time. This rough texture created discomfort by some users. This roughness is caused by a top layer of the fabric being an absorbent rayon-polyester blend that is not heat-treated. Therefore, the '281 pad included a top layer of woven polyester or polyester tricot mesh to provide a smooth patient contact surface. However, this adds to the expense in manufacturing the pad, due to the extra layer of fabric and the need for bonding it to the second absorbent layer.

In a further improvement to the art, U.S. Pat. No. 4,943,286 issued to Armstead on Jul. 24, 1990, disclosed a washable and reusable patient underpad is formed of four separate layers: a top layer (patient-contact) of absorbent polyester-rayon needle form non-woven fabric; a second layer of non-woven polyester; a third layer of synthetic water impervious material; and a fourth layer of synthetic fleece warp knit fabric. The second, third and fourth layers are bonded together.

The underpad of the present invention provides improved softness, drying time, absorbency, and patient comfort over previous underpad constructions.

SUMMARY OF THE INVENTION

The present invention is directed to a reusable patient underpad having a top section preferably constructed from a porous terry or circular knit fabric with a circular knit polyester stabilizing yarn backing. The face yarn of the top section is a blend of acrylic fibers and absorbent fibers (cotton or rayon, for example). A bottom section is preferably constructed from PVC vinyl bonded to a polyester knit cloth. The top and bottom sections are joined at their respective edges by serging, stitching, or binding tape.

In a preferred embodiment of the invention, the porous knit fabric of the top section is oriented such that the fabric "loops" are facing the bottom section so that the underpad will dry more quickly.

In another embodiment of the underpad, the top section is made of a porous fleece-type fabric.

In yet another embodiment, the porous fabric layer of the top section is a porous woven material.

In a further embodiment, an antimicrobial agent is incorporated into the acrylic fibers of the top layer for continued antimicrobial action.

The fabric construction of the underpad increases absorbency and patient comfort, while decreasing drying time.

DESCRIPTION OF THE PREFERRED EMBODIMENTS

Figure 1:
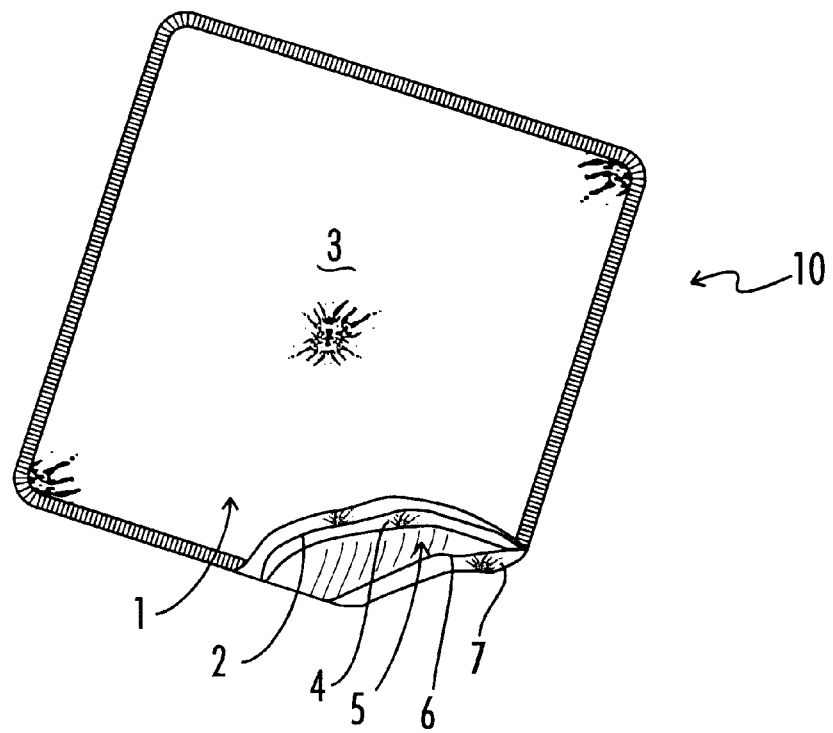
FIG. 1 is a perspective view of the underpad of the present invention with a partial cut-away and cross-section showing the various material layers.
Figure 2:
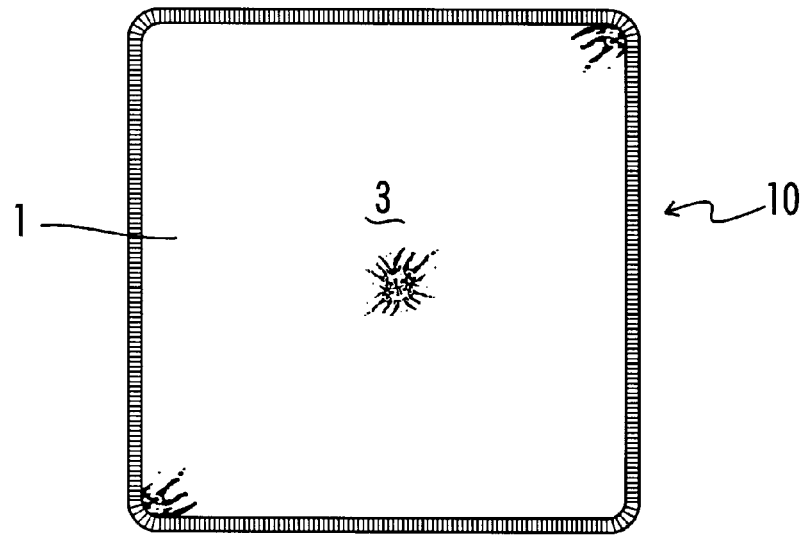
FIG. 2 is a top view of the underpad of FIG. 1 showing the patient contact surface of the top section and the stitching around the edges of the pad.

As shown in FIGS. 1 and 2, the patient underpad 10 of this invention has an top section 1 joined to a bottom section 5. In use, the top section 1 will be proximal the patient (not shown) and the bottom section 5 will be in contact with the bed or bedding. The top section 1 includes a porous knit fabric layer 2 having an outer patient contact surface 3 and preferably made from a terry or circular knit fabric. The top section 1 and porous fabric layer 2 are stabilized on a back surface by a fabric backing stabilizing layer 4, preferably made from a circular knit U.L.S. polyester yarn. Such a yarn can be obtained from Unifi Corp. of North Carolina. The bottom section 5 includes a water barrier 6, preferably made from PVC vinyl, bonded to a polyester knit cloth 7 that is in contact with the patient's bed (not shown). A suitable PVC vinyl material is 8/28 available from Vintex, Inc. of Ontario, Canada.

In a further embodiment of the invention, the face yarn of the knit fabric layer 2 may be blend of acrylic or polyester fibers and absorbent fibers of cotton, rayon, or other absorbent material. In a preferred embodiment, the knit fabric layer 2 is made of a course-cut terry loop 6.0 mm sinker.

In an alternate embodiment, the knit fabric layer 2 of the top section 1 can be fleeced for added softness. Also, a porous woven fabric can be used in place of the terry or fleece, but with a corresponding reduction in fabric stretch and porosity. In a further embodiment, an antimicrobial agent may be incorporated into the acrylic fibers of the knit fabric layer 2 for continued antimicrobial action.

Those skilled in the art will recognize that a terry or circular knit fabric is characterized by a having a plurality of loops extending away from a smooth fabric surface. In a preferred embodiment, the terry loops or circular knit loops of the knit fabric layer 2 are oriented downward, away from the patient and facing the interior of the underpad construction. This provides a path for increased air circulation under the patient between the top section 1 and bottom section 5, thereby reducing drying time. In an alternate embodiment, the terry loops or circular knit of the knit fabric layer 2 are oriented upward so that they are on the patient contact surface 3.

The knit fabric used in the knit fabric layer 2 may be finished by bleaching and framing, or by napping, followed by heat setting, if needed to relax the fabric. In one embodiment, the top section 1 may be attached to the bottom section 5 by surging. In an alternate embodiment, the top section 1 may be attached by binding the edges of the knit fabric layer 2 to the edges of the bottom section 5.

In a further embodiment, the top section 1 may be stitched around edge 8 to the bottom section 5 with the terry or circular loops of the knit fabric layer 2 oriented inward toward the water barrier 6. In another embodiment, top section 1 may be stitched around edge 8 to the bottom section 5 with the terry or circular loops oriented outward from the water barrier 6.

In yet another embodiment of the invention, the nap side of the knit fabric layer 2 may be oriented upward and away from the water barrier 6 when stitched to the bottom section 5. In a further embodiment, the nap side of the knit fabric layer 2 may be oriented downward and toward the water barrier 6 when stitched to the bottom section 5.

A patient underpad constructed in accordance with this invention will have improved softness and pliability to add to the patient's comfort level. Air circulation under the patient is also enhanced from the terry fabric, aiding in drying. The pad will be easier to clean because of the porous knit fabric.

Thus, although there have been described particular embodiments of the present invention of a new and useful Patient Underpad, it is not intended that such references be construed as limitations upon the scope of this invention except as set forth in the following claims.

What is claimed is:

1. A reusable patient underpad comprising:
   (a) a top section comprising a porous fabric layer defining a patient contact surface, the porous fabric layer joined to an inner stabilizing layer; and
   (b) the top section attached to a bottom section, the bottom section including a water barrier.

2. The underpad of claim 1 wherein the porous fabric layer is a terry knit fabric.

3. The underpad of claim 2 wherein the terry knit fabric has terry loops oriented toward the bottom section.

4. The underpad of claim 2 wherein the terry knit fabric has terry loops oriented upward from the patient contact surface.

5. The underpad of claim 1 wherein the porous fabric layer is a circular knit fabric.

6. The underpad of claim 1, the water barrier comprising PVC vinyl.

7. The underpad of claim 6, the bottom section further comprising a polyester knit cloth bonded to the PVC vinyl.

8. The underpad of claim 1 wherein the porous fabric layer comprises a blend of acrylic fibers and absorbent fibers.

9. The underpad of claim 8 further comprising an antimicrobial compound incorporated into the acrylic fibers.

10. A reusable patient underpad comprising:
    (a) a porous fabric layer having an outer patient contact surface and a stabilizing yarn on a back surface; and
    (b) a water barrier attached to the porous fabric layer.

11. The patient underpad of claim 10 wherein the porous fabric layer comprises a circular knit fabric.

12. The patient underpad of claim 10 wherein the porous fabric layer comprises a terry knit fabric.

13. The patient underpad of claim 12 wherein the stabilizing yarn comprises a circular knit polyester.

14. The patient underpad of claim 13 wherein the terry knit fabric has loops oriented toward the water barrier to create an air flow path between the terry knit fabric and the water barrier.

15. The patient underpad of claim 14 further comprising a polyester knit cloth joined to the water barrier.

\* \* \* \* \*